US012569160B2

(12) United States Patent
Kodama et al.

(10) Patent No.: US 12,569,160 B2
(45) Date of Patent: Mar. 10, 2026

(54) SYSTEM AND METHOD FOR DETECTING POSITION OF LONG MEDICAL DEVICE

(71) Applicant: ASAHI INTECC CO., LTD., Seto (JP)

(72) Inventors: Seigo Kodama, Chiryu (JP); Takeshi Sato, Chiryu (JP); Joji Isozumi, Chiryu (JP); Yasuhiro Yamashita, Chiryu (JP); Makoto Nishiuchi, Seto (JP); Manabu Shimogami, Seto (JP); Fumiyoshi Oshima, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 8 days.

(21) Appl. No.: 17/884,177

(22) Filed: Aug. 9, 2022

(65) Prior Publication Data

US 2022/0378317 A1      Dec. 1, 2022

Related U.S. Application Data

(63) Continuation of application No. PCT/JP2020/005819, filed on Feb. 14, 2020.

(51) Int. Cl.
A61B 5/06 (2006.01)
A61B 8/12 (2006.01)

(52) U.S. Cl.
CPC . A61B 5/06 (2013.01); A61B 8/12 (2013.01)

(58) Field of Classification Search
CPC .......... A61B 5/06; A61B 8/12; A61B 5/7425; A61B 8/0841; A61B 8/085; A61B 8/0891; A61B 8/4218; A61B 8/54; A61B 5/061
See application file for complete search history.

(56) References Cited

U.S. PATENT DOCUMENTS

| | | | |
|---|---|---|---|
| 5,307,816 A * | 5/1994 | Hashimoto | ........ A61B 17/2258 600/463 |
| 6,711,433 B1 * | 3/2004 | Geiger | .................. G06T 11/008 378/98.12 |
| 2004/0143183 A1 | 7/2004 | Toyoda et al. | |
| 2004/0176683 A1 * | 9/2004 | Whitin | ................... A61B 5/068 600/117 |
| 2005/0099290 A1 | 5/2005 | Govari | |
| 2007/0093710 A1 | 4/2007 | Maschke | |
| 2008/0294034 A1 | 11/2008 | Krueger et al. | |
| 2009/0062782 A1 * | 3/2009 | Brown | ................... A61B 18/20 606/15 |
| 2010/0063400 A1 | 3/2010 | Hall et al. | |

(Continued)

FOREIGN PATENT DOCUMENTS

| | | | |
|---|---|---|---|
| JP | 2004-215992 A | 8/2004 | |
| JP | 2005-144169 A | 6/2005 | |

(Continued)

*Primary Examiner* — Hien N Nguyen
(74) *Attorney, Agent, or Firm* — Oliff PLC

(57) ABSTRACT

A system for detecting a position of a long medical device includes a model acquisition portion that acquires a blood vessel model, a correspondence detection portion 1 that detects a position of a long medical device inserted into a blood vessel and detects a correspondence between the blood vessel model and the position of the long medical device, and a display portion that displays the position of the long medical device in association with the blood vessel model on the basis of a detection result of the correspondence detection portion.

14 Claims, 15 Drawing Sheets

(56)                References Cited

U.S. PATENT DOCUMENTS

| | | | |
|---|---|---|---|
| 2010/0174196 A1* | 7/2010 | Ryan ....................... | A61F 2/958 |
| | | | 623/1.11 |
| 2014/0155768 A1* | 6/2014 | Orion .................. | A61B 5/0215 |
| | | | 600/300 |
| 2014/0304184 A1* | 10/2014 | Fletcher ................. | G06Q 10/00 |
| | | | 705/325 |
| 2016/0100772 A1 | 4/2016 | Ikuma et al. | |
| 2016/0331469 A1* | 11/2016 | Hall ......................... | A61B 8/12 |
| 2018/0214241 A1 | 8/2018 | Furuta et al. | |

FOREIGN PATENT DOCUMENTS

| | | |
|---|---|---|
| JP | 2007-523699 A | 8/2007 |
| JP | 2010-057910 A | 3/2010 |
| JP | 5815156 B2 | 11/2015 |
| JP | 2019-042519 A | 3/2019 |
| WO | 2019/097317 A1 | 5/2019 |

* cited by examiner

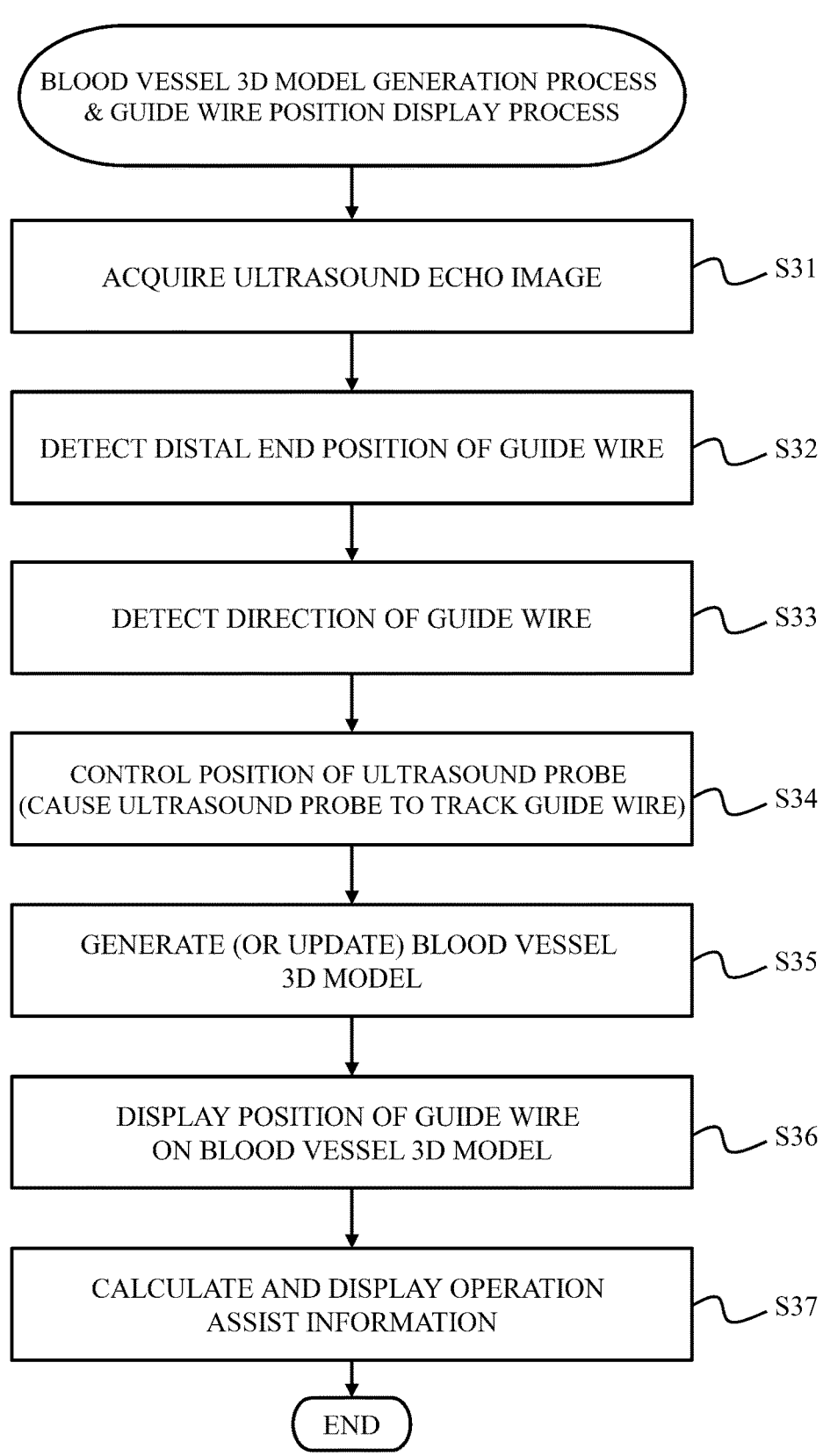

BLOOD VESSEL 3D MODEL GENERATION PROCESS
& GUIDE WIRE POSITION DISPLAY PROCESS

ACQUIRE ULTRASOUND ECHO IMAGE — S31

DETECT DISTAL END POSITION OF GUIDE WIRE — S32

DETECT DIRECTION OF GUIDE WIRE — S33

CONTROL POSITION OF ULTRASOUND PROBE
(CAUSE ULTRASOUND PROBE TO TRACK GUIDE WIRE) — S34

GENERATE (OR UPDATE) BLOOD VESSEL
3D MODEL — S35

DISPLAY POSITION OF GUIDE WIRE
ON BLOOD VESSEL 3D MODEL — S36

CALCULATE AND DISPLAY OPERATION
ASSIST INFORMATION — S37

END

SYSTEM AND METHOD FOR DETECTING POSITION OF LONG MEDICAL DEVICE

This application is a continuation application of International Application No. PCT/JP2020/005819, filed Feb. 14, 2020. The contents of this application are incorporated herein by reference in their entirety.

TECHNICAL FIELD

Disclosed embodiments relate to a system and a method for detecting a position of a long medical device.

BACKGROUND ART

When treating with a catheter, a doctor recognizes a shape of a blood vessel from an X-ray image obtained by injecting a contrast medium into the blood vessel, and inserts, based on the recognition result, a long medical device such as a guide wire into the blood vessel. However, it is difficult for the doctor to know in real time where the guide wire is currently located inside the blood vessel and whether the guide wire stays out of the blood vessel.

Therefore, there is proposed a technique for measuring the position of the guide wire by fixing a permanent magnet to a distal end of the guide wire and detecting magnetism with a plurality of magnetic sensors provided around a head of a subject (Patent Literature 1). It is possible to display the measured position of the guide wire to be superimposed on a blood vessel image acquired by magnetic resonance imaging (MRI).

CITATION LIST

Patent Literature

Patent Literature 1: Japanese Unexamined Patent Application Publication No. 2004-215992

SUMMARY

Technical Problem

In the conventional technology, it is necessary to obtain a map in which a relationship between the magnetism detected by each magnetic sensor and a position and a direction of a permanent magnet at the distal end of the catheter is measured in advance, and thus, it requires great care. The conventional technology is for measuring the position of the catheter at a head where the X-ray image is obtained with difficulty but is not for detecting the position of the catheter at a location other than the head.

Disclosed embodiments have been made in view of the above problems, and an object thereof is to provide an easy-to-use system and method for detecting a position of a long medical device.

Solution to Problem

To resolve the above problems, a system for detecting a position of a long medical device according to one aspect of disclosed embodiments includes a model acquisition portion that acquires a blood vessel model, a correspondence detection portion that detects a position of a long medical device inserted into a blood vessel and detects a correspondence between the blood vessel model and the position of the long medical device, and a display portion that displays the position of the long medical device in association with the blood vessel model on the basis of a detection result of the correspondence detection portion.

The correspondence detection portion may detect the position of the long medical device by radio waves.

The correspondence detection portion may include a plurality of radio wave reception portions arranged around a subject and a radio wave transmission portion provided in the long medical device.

The correspondence detection portion may include a plurality of radio wave transmission portions arranged around the subject and a radio wave reception portion provided at a distal end of the long medical device.

The correspondence detection portion may include an ultrasound imaging device with an ultrasound probe, and an operation portion that operates the ultrasound probe by pressing the ultrasound probe against a surface of the subject. The model acquisition portion may obtain a blood vessel model generated based on an ultrasound echo image obtained by the ultrasound probe. The correspondence detection portion may recognize the long medical device and the blood vessel from the ultrasound echo image obtained by the ultrasound probe and cause the ultrasound probe to follow a movement of the recognized long medical device to detect the correspondence between the blood vessel model and the long medical device.

When the ultrasound probe is caused to follow the movement of the distal end of the long medical device, the blood vessel model may be reconstructed.

The correspondence detection portion may include a blood vessel characteristic point detection portion that detects a characteristic point of a blood vessel, and a comparison portion that calculates the position of the long medical device by comparing a characteristic point detected by the blood vessel characteristic point detection portion and a characteristic point included in the blood vessel model.

The correspondence detection portion may detect the correspondence between the blood vessel model and the position of the long medical device from a feed rate of the long medical device into the blood vessel.

The correspondence detection portion may detect the correspondence between the blood vessel model and the position of the long medical device from a feed rate and a direction of the long medical device into the blood vessel.

The correspondence detection portion may include a first detection portion that detects a predetermined range including the position of the long medical device in the blood vessel model and a second detection portion that detects a correspondence between the blood vessel model and the position of the long medical device within the predetermined range detected by the first detection portion.

The first detection portion may detect the predetermined range based on the feed rate of the long medical device into the blood vessel, and the second detection portion may include a blood vessel characteristic point detection portion that detects a characteristic point of a blood vessel, and a comparison portion that calculates the position of the long medical device by comparing a characteristic point detected by the blood vessel characteristic point detection portion and a characteristic point included in the blood vessel model.

The correspondence detection portion may calculate a predetermined value from the correspondence between the blood vessel model and the position of the long medical device, and the display portion may display the calculated predetermined value in association with the position of the long medical device, on the blood vessel model.

The predetermined value may be a distance between the position of the long medical device in the blood vessel model and a blood vessel wall.

An alarm may be output when the predetermined value reaches a previously set threshold value.

According to disclosed embodiments, it is possible to display a blood vessel model in association with the position of a long medical device.

BRIEF DESCRIPTION OF DRAWINGS

FIG. 7 is a flowchart of a guide wire position display process and the like.

FIG. 8 is another flowchart of the guide wire position display process and the like.

FIG. 11 is a flowchart of a guide wire position display process and the like.

FIG. 13 is a flowchart of a guide wire position display process and the like.

DETAILED DESCRIPTION OF EMBODIMENTS

In the present embodiment, examples of a long medical device to be inserted into a blood vessel include a guide wire, a guiding catheter, a microcatheter, a balloon catheter, a cutting balloon, and a stent delivery device.

An embodiment of disclosed embodiments will be described, based on the drawings, as an example of a case where the long medical device is a guide wire, below. In the present embodiment, when a relationship between a position of the guide wire and a blood vessel model is displayed, convenience for a doctor or an operator (hereinafter referred to as "doctor and the like") is improved.

Figure 1:
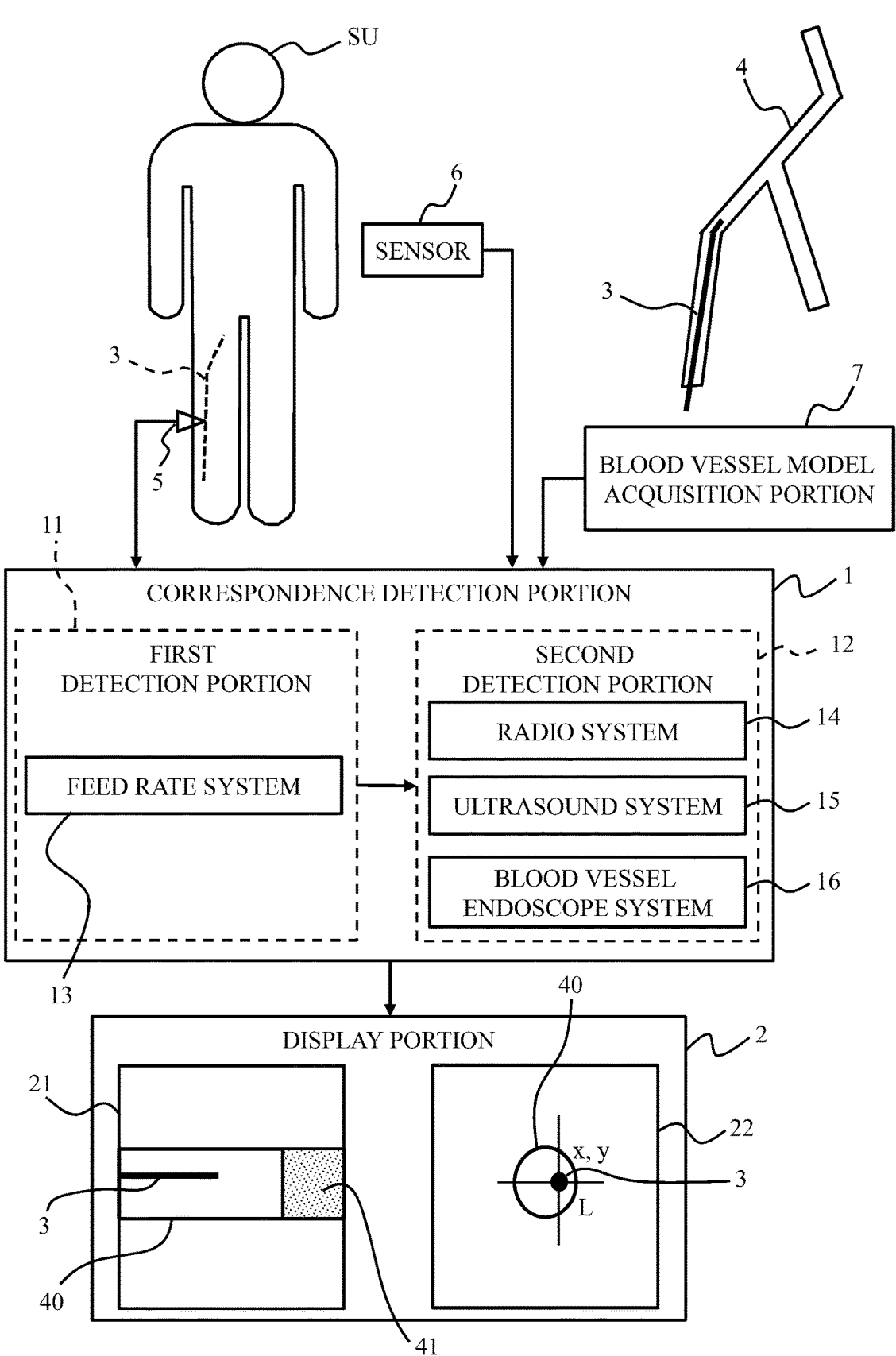
FIG. 1 is an explanatory diagram illustrating an outline of the present embodiment.

With reference to FIG. 1, an outline of according to the present embodiment will be described. A plurality of other embodiments included in the present embodiment will be described later with reference to other drawings. FIG. 1 illustrates an outline of the present embodiment and does not define the scope of disclosed embodiments. Disclosed embodiments may be configured from a part of the configurations disclosed in FIG. 1, or disclosed embodiments may be configured by including a configuration not disclosed in FIG. 1.

A system for detecting a position of a guide wire according to the present embodiment may include a correspondence detection portion 1, a display portion 2, sensors 5 and 6, and a blood vessel model acquisition portion 7, for example. The sensor 5 may be called a first sensor 5 used by a first detection portion 11, and the sensor 6 may be called a second sensor 6 used by a second detection portion 12.

The blood vessel model acquisition portion 7 acquires a blood vessel model 4 of a subject SU created before or during a surgery and supplies such a model to the correspondence detection portion 1. The blood vessel model 4 may be generated by, for example, an ultrasound imaging device or an X-ray computed tomography (CT) device. The blood vessel model 4 may be a three-dimensional model or a two-dimensional model. The correspondence detection portion 1 may appropriately use the three-dimensional model and the two-dimensional model.

The correspondence detection portion 1 detects a position of the guide wire 3 inserted into a blood vessel of the subject SU, and detects a correspondence between the blood vessel model 4 and the guide wire 3. The correspondence is, for example, the position of the guide wire 3 in the blood vessel model 4. The subject SU is usually a human, but may be a non-human subject such as an animal.

The correspondence detection portion 1 may include the first detection portion 11 and the second detection portion 12. The first detection portion 11 detects a predetermined range in which the guide wire 3 is estimated to exist (predetermined range including a distal end portion of the guide wire, for example), according to a function of a feed rate system 13. That is, the first detection portion 11 detects, based on a signal from a feed rate detection sensor 5 that detects a feed rate of the guide wire 3 into the blood vessel of the subject SU, a predetermined range in which the position of the guide wire 3 is estimated to exist in the blood vessel model 4. The second detection portion 12 utilizes a signal from another sensor 6, according to a function of at least any one of a radio system 14, an ultrasound system 15, and a blood vessel endoscope system 16, to detect the positional relationship between the blood vessel model 4 and the guide wire 3 in the predetermined range detected by the first detection portion 11. The other sensor 6 includes an antenna for transmitting or receiving radio waves, an ultrasound probe, and a vascular endoscope, as described later.

The display portion 2 displays a detection result of the correspondence detection portion 1 on a screen to provide information to the doctor and the like. The display portion 2 may provide a relationship between the blood vessel and the guide wire 3 to the doctor and the like from a plurality of viewpoints. For example, the display portion 2 may include a first display portion 21 that displays a longitudinal cross section of a blood vessel and a second display portion 22 that displays a transverse cross section of the blood vessel.

In the first display portion 21, for example, in the longitudinal cross section of the blood vessel 40, a positional relationship between an affected part (lesion) 41 to be treated and the guide wire 3 is displayed. In the second display portion 22, in the transverse cross section of the blood vessel 40, a positional relationship between the inner wall of the blood vessel 40 and the guide wire 3 is displayed. A viewpoint illustrating the positional relationship between the blood vessel 40 and the guide wire 3 is not limited to the longitudinal cross section or the transverse cross section. The display portion 2 may display the positional relationship between the blood vessel 40 and the guide wire 3 from any viewpoint desired by the doctor and the like.

In the explanatory diagram of FIG. 1, the following method is disclosed. That is, a method for detecting the position of the guide wire 3 from the feed rate of the guide wire 3 to the blood vessel and the blood vessel model (function 13), a method for detecting the position of the guide wire 3, based on a transmission and reception state between an antenna provided in the guide wire 3 and an antenna provided around the subject SU and the blood vessel model (function 14), a method for detecting the position of the guide wire 3 by using an ultrasound imaging device (function 15), a method for detecting the position of the guide wire 3, based on an image obtained from an endoscope inserted into the blood vessel and the blood vessel model (function 16), a combination of the function 13 and the function 14, a combination of the function 13 and the function 15, a combination of the function 13 and the function 16, a combination of function 13, the function 14, and the function 15, a combination of function 13, the function 14, and the function 16, a combination of function 13, the function 15, and the function 16, and a combination of functions 13, 14, 15, and 16. When a plurality of different methods (functions) are appropriately used, it is possible to detect the position of the guide wire 3 and display such a position on the blood vessel model 4.

According to the present embodiment configured as described above, contrary to the conventional technology, there is no need to previously acquire the signal of each magnetic sensor according to the position and an orientation of the permanent magnet to generate a map, and thus, it is possible to detect the position of the guide wire 3 more easily than the conventional technology and display the position of the guide wire 3 in association with the blood vessel model 4.

If the function 14 is used in the present embodiment, it is possible to make a measurement distance longer and to improve the convenience. As described later, when some reference points are simply measured by using a marker as described later, it is possible to specify the correspondence between the blood vessel and the guide wire 3.

If the function 15 is used in the present embodiment, as described later, it is possible to generate the blood vessel model 4 by operating the ultrasound probe to press the ultrasound probe against the surface of a body, as described later, and to simultaneously detect the blood vessel and the guide wire 3 by the ultrasound probe during the surgery, and thus, it is possible to detect and display the relationship between the blood vessel and the guide wire 3.

If the function 16 is used in the present embodiment, the characteristic point is obtained from an image displaying a shape of an internal blood vessel and such a characteristic point and the characteristic point of the blood vessel model are compared and collated to specify the positional relationship between the guide wire 3 and the blood vessel model 4. Therefore, it is not necessary to arrange a sensor or place a marker outside a patient, and it is possible to more easily detect and display the relationship between the guide wire 3 and the blood vessel.

If the function 13 is used in the present embodiment, it is possible to specify a predetermined range where the guide wire exists in a short period of time. Therefore, as in a case where the function 13 and the function 16 are combined, it is possible to more accurately measure an area within the predetermined range specified by the feed rate system by another system. As a result, it is possible to detect the position of the guide wire quickly and in a short period of time.

First Embodiment

Figure 2:
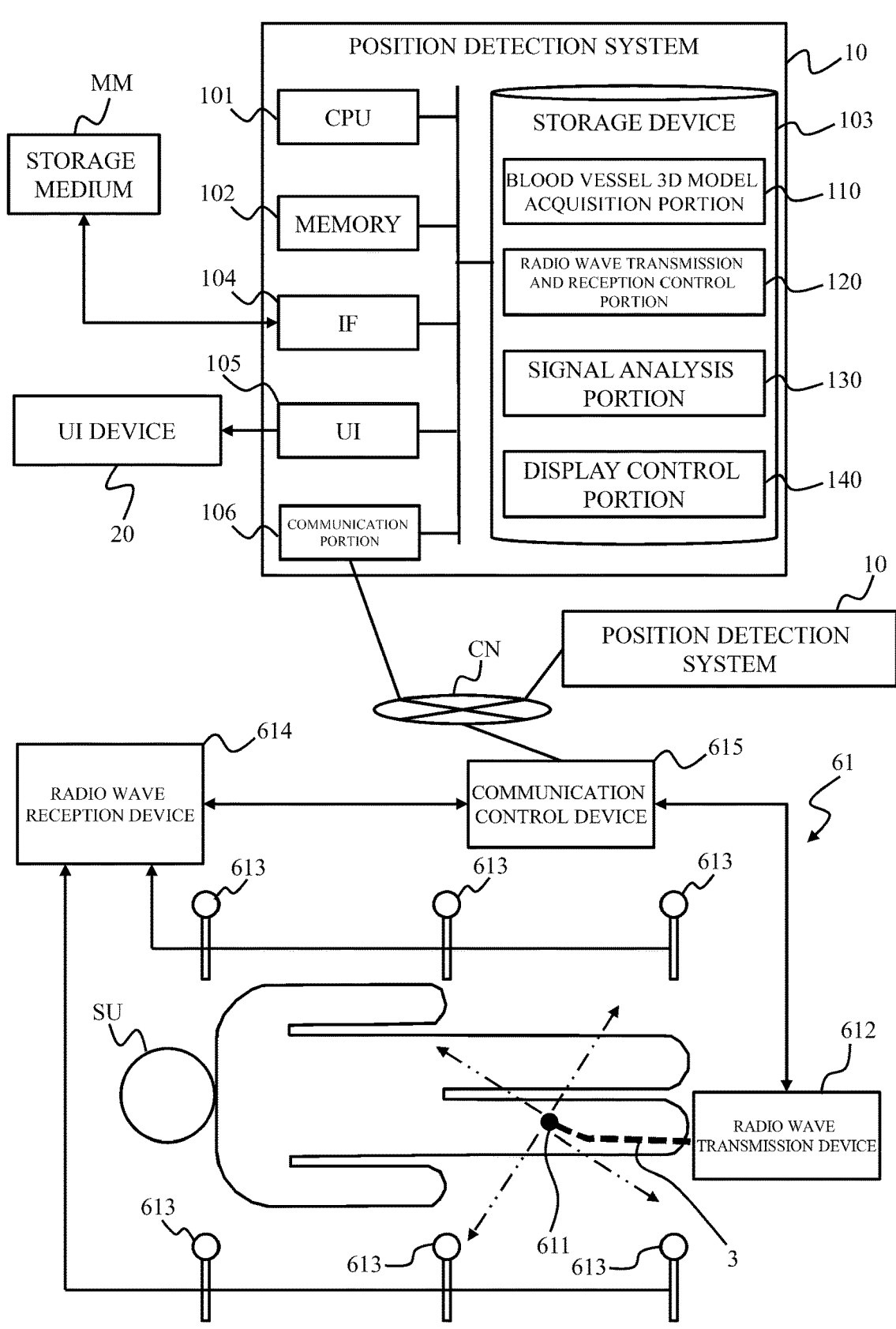
FIG. 2 is an explanatory diagram illustrating an example of a configuration of a first embodiment.
Figure 3:
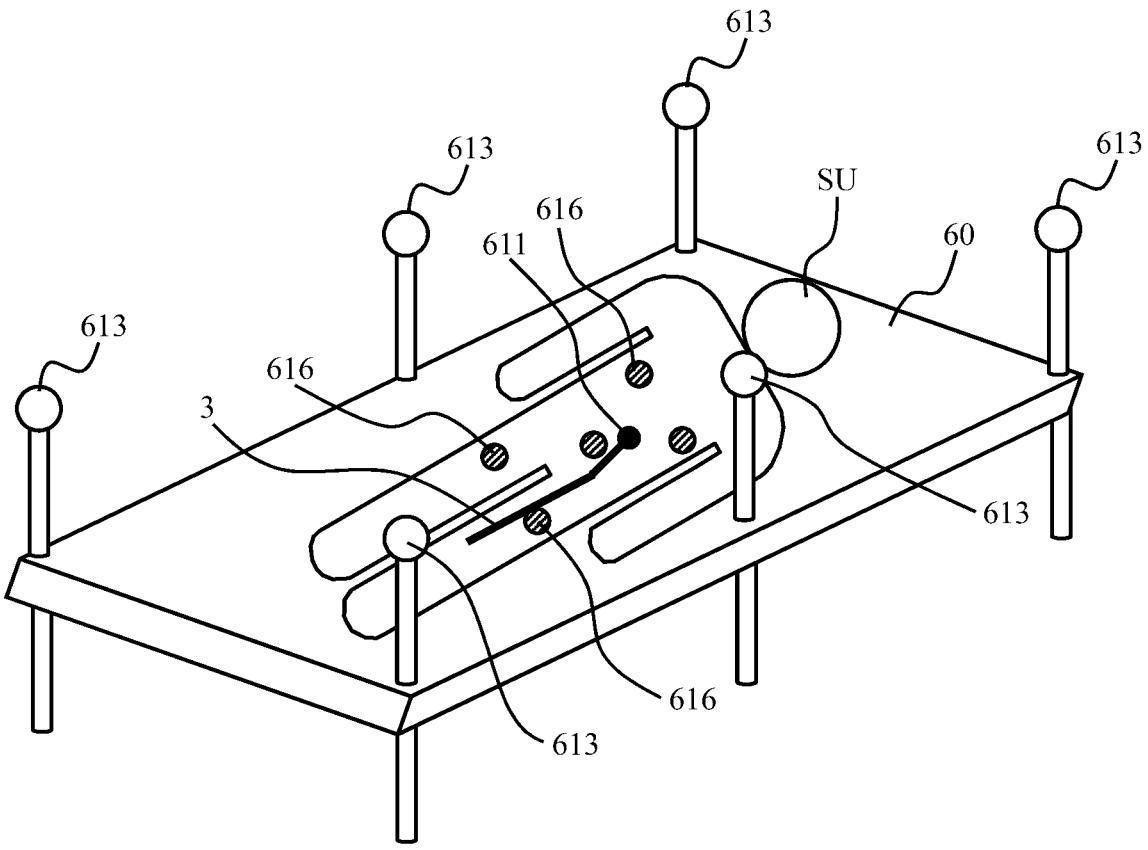
FIG. 3 is an explanatory diagram illustrating an arrangement relationship of an antenna between a distal end of a guide wire and an area around a subject.

A first embodiment will be described with reference to FIGS. 2 to 4. FIG. 2 illustrates an example of a configuration of a method (function) 14 for detecting the position of the guide wire 3 using radio waves.

In the first embodiment, for example, at least one position detection system 10 and a sensing system 61 using radio waves are provided. The sensing system 61 using radio waves is one example where the function 14 is realized and includes a radio wave transmission antenna 611 being an example of a "radio wave transmission portion", a radio wave transmission device 612 being an example of a "radio wave transmission portion", a plurality of radio wave reception antennas 613 being an example of a "radio wave reception portion", a radio wave reception device 614 being an example of a "radio wave reception portion", and a communication control device 615, for example.

Firstly, the position detection system 10 will be described. The position detection system 10 is an example where the correspondence detection portion 1 described in FIG. 1 is realized. The position detection system 10 includes a microprocessor (in FIG. 2, CPU: Central Processing Unit) 101, a memory 102, a storage device 103, a medium interface 104, a user interface 105, and a communication portion 106, for example. The position detection system 10 may be a dedicated device provided with a dedicated circuit, or may be a general-purpose computer for executing a predetermined computer program. The position detection system 10 may establish linkage among a plurality of devices. For example, one or more position detection systems 10 may be generated by coordinating a plurality of computers.

The position detection system 10 may include a plurality of the position detection systems 10. That is, one radio wave type sensing system 61 and the plurality of position detection systems 10 may be connected to enable bidirectional communication via a communication network CN. As a result, for example, it is possible to arrange one position detection system 10 in a surgery room, and another position detection system 10 at a place away from the surgery room, and thus, it is possible to simultaneously share the position of the guide wire 3 among the plurality of position detection systems 10.

As a result of causing predetermined computer programs 110 to 140 stored in the storage device 103 to be read and executed into the memory 102, the microprocessor 101 realizes each function as the position detection system 10.

The storage device 103 stores therein a blood vessel 3D model acquisition portion 110, a radio wave transmission and reception control portion 120, a signal analysis portion 130, a display control portion 140, and an unillustrated operating system, for example. The blood vessel 3D model acquisition portion 110 is a function of acquiring a blood vessel 3D model (stereoscopic blood vessel model) as an example of the blood vessel model 4. The radio wave transmission and reception control portion 120 is a function of controlling transmission (output) of radio waves from the antenna 611 of the guide wire 3 and reception of radio waves from each antenna 613. The signal analysis portion 130 is a function of calculating the position of the guide wire 3 by analyzing the radio wave signal received by each antenna 613. The display control portion 140 is a function of displaying the correspondence between the position of the guide wire 3 and the blood vessel 3D model 4 on a user interface device 20.

The medium interface 104 is a circuit used to communicate data with a storage medium MM such as a semiconductor memory or a hard disk. It is possible to store at least some of the predetermined computer programs 110 to 140 into the storage medium MM and install the stored computer programs into the storage device 103 from the storage medium MM. Alternatively, it is possible to transfer at least some of the predetermined computer programs 110 to 140 stored in the storage device 103 to the storage medium MM and store therein such programs. Instead of the storage medium MM, the communication network CN may be employed for a transmission medium for predetermined computer programs. The data calculated by one position detection system 10 may be transmitted to another position detection system 10 via the communication network CN.

The user interface device 20 exchanges information with the position detection system 10 via the user interface 105. The user interface device 20 includes an information input device and an information output device. The information input device and the information output device may be provided in one device. Examples of the information input device include a keyboard, a push button, a voice input device, a touch panel, and a pointing device such as a mouse. Examples of the information output device include a monitor display, a printer, a voice synthesizer, and a light.

The communication portion 106 performs bidirectional communication with the communication network CN. The position detection system 10 may communicate with the radio wave type sensing system 61 and another position detection system 10 by the communication portion 106 and the communication network CN.

An example of a configuration of the radio wave type sensing system 61 will be described. The radio wave transmission antenna 611 is an antenna provided at a predetermined position of the guide wire 3, and transmits radio waves from the radio wave transmission device 612 toward surrounding areas. The radio wave transmission antenna 611 may be attached to, for example, the distal end portion of the guide wire 3 or a certain location around the distal end portion thereof. The radio wave transmission antenna 611 may also be attached to a region other than the distal end portion of the guide wire 3.

The radio wave reception antenna 613 includes a plurality of the radio wave reception antennas 613, and the plurality of such antennas 613 are arranged around the subject SU. As illustrated in FIG. 3, each radio wave reception antenna 613 is attached to a predetermined position located around a bed 60 placed thereon with the subject SU. The radio waves transmitted from the radio wave transmission antenna 611 of the guide wire 3 are received by each radio wave reception antenna 613, and the received signals are forwarded from the radio wave reception device 614 to the communication network CN via the communication control device 615, and received by the position detection system 10.

Depending on a distance and a direction between the radio wave transmission antenna 611 of the guide wire 3 and each radio wave reception antenna 613, an arrival time and an intensity of the radio wave signal received by each radio wave reception antenna 613 are different. Therefore, for example, by using a method such as three-point positioning, the signal analysis portion 130 may specify the position of the radio wave transmission antenna 611. For example, a beacon positioning method such as Bluetooth Low Energy (BLE) may be used. In the present embodiment, a type, a wavelength, and the like of the radio wave transmission device and the radio wave reception device are not limited.

In a predetermined space defined by the arrangement position of each radio wave reception antenna 613, the position of the radio wave transmission antenna 611 is detected. When the blood vessel 3D model 4 of the subject SU is generated, if a radio wave transmission type marker 616 is attached to a specific position of the subject SU to transmit radio waves, it is possible to specify the positional relationship between the blood vessel 3D model 4 and the marker 616. As a result, it is possible to assign the blood vessel 3D model 4 to the predetermined space defined by the arrangement position of each radio wave reception antenna 613. Therefore, the signal analysis portion 130 may analyze the correspondence (positional relationship) between the position of the radio wave transmission antenna 611 and the blood vessel 3D model 4.

Figure 4:
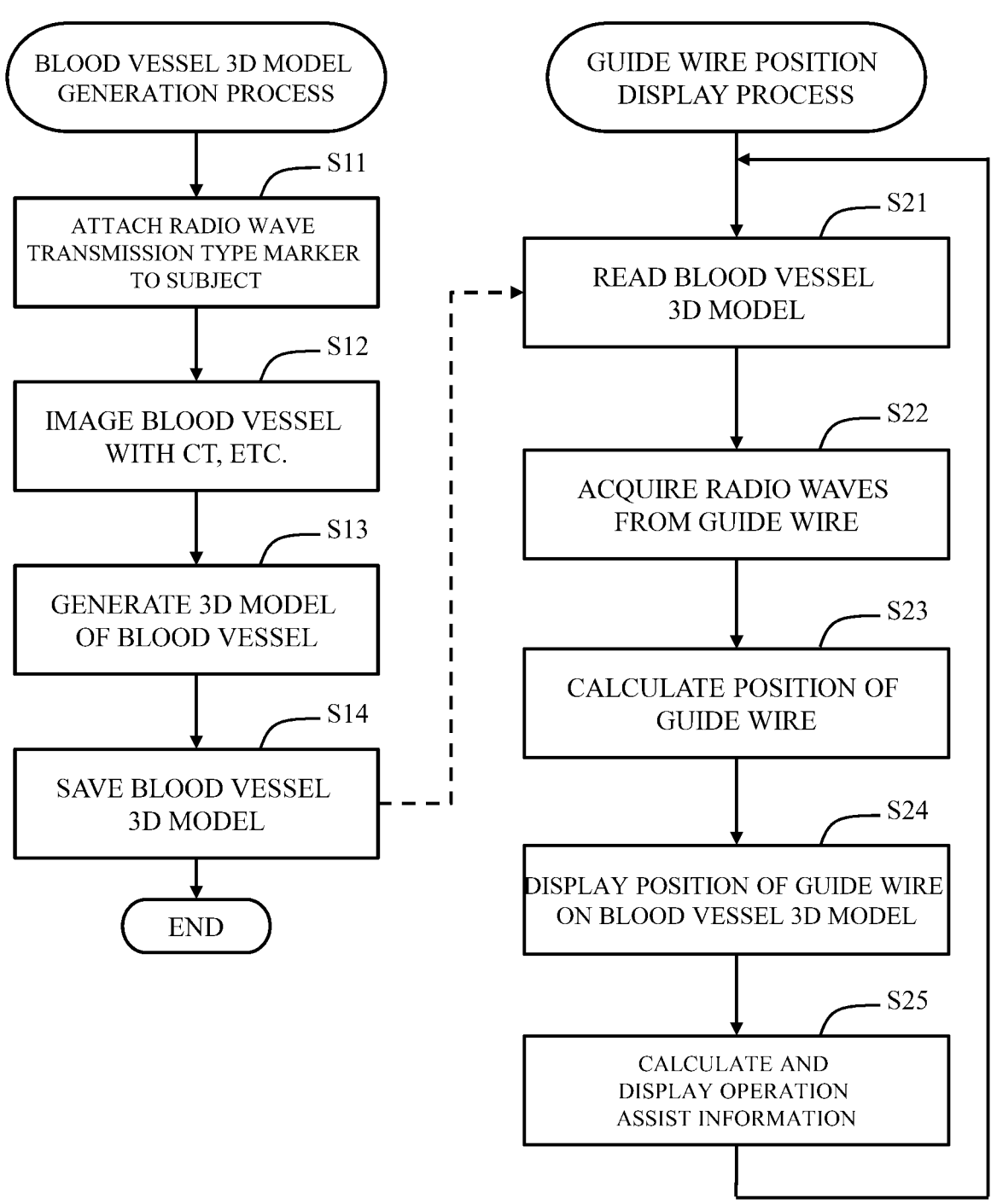
FIG. 4 is a flowchart of a blood vessel model generation process and a guide wire position display process.

With reference to FIG. 4, a process of generating the blood vessel 3D model and a process of displaying the position of the guide wire on the blood vessel 3D model will be described.

In a blood vessel 3D model generation process illustrated on the left side in FIG. 4, the radio wave transmission type marker 616 is attached to a predetermined position of the subject SU (S11). Such an attachment task may be performed manually by a human such as a doctor or an operator, or may be automatically performed by a robot hand.

In step S12, a practitioner such as a doctor images the blood vessel of the subject SU by using an X-ray CT device (not illustrated). Similarly to the process in step S11, the blood vessel of the subject SU may be automatically imaged by a robot.

The blood vessel 3D model 4 of the subject SU is generated from image data imaged in step S12 (S13) and saved in an unillustrated storage device (S14). The blood vessel 3D model 4 generated in step S13 also includes information on the radio wave transmission type marker 616.

The blood vessel 3D model acquisition portion 110 of the position detection system 10 acquires the data of the blood vessel 3D model 4 saved in step S14 (S21). The radio wave transmission and reception control portion 120 of the position detection system 10 acquires signals from each radio wave reception antenna 613 via the radio wave reception device 614, the communication control device 615, the communication network CN, and the communication portion 106 (S22).

The signal analysis portion 130 of the position detection system 10 calculates the position of the guide wire 3 (for example, the distal end position of the guide wire 3), based on the signal from each radio wave reception antenna 613 (S23). More particularly, the signal analysis portion 130 calculates the position of the radio wave transmission antenna 611 attached to the guide wire 3, but for the signal analysis portion 130, the relationship between the attachment position of the antenna 611 and the distal end position of the guide wire 3 is well-known, and thus, it is possible to evaluate the distal end position of the guide wire 3 from the position of the antenna 611.

The display control portion 140 of the position detection system 10 generates a screen on which to display the position of the guide wire 3 in association with the blood vessel 3D model 4, and outputs such a screen to the user interface device 20 (S24).

The display control portion 140 of the position detection system 10 calculates operation assist information as an example of a "predetermined value" and displays such information on an image indicating the correspondence between the blood vessel 3D model 4 and the guide wire 3 (S25). The operation assist information is information available to assist the operation of the guide wire 3 by the doctor and the like. Examples of the operation assist information include the distance or the angle between the guide wire 3 and the inner wall of the blood vessel, as described in FIG. 1. The operation assist information may also include a relationship with a threshold value set to the blood vessel 3D model 4. That is, the position detection system 10 may output an alarm if the distal end of the guide wire 3 reaches a position of a predetermined threshold value from the inner wall of the blood vessel.

According to the present embodiment configured as described above, the position of the guide wire 3 is detected by using radio waves, and thus, it is possible to make a measurable distance longer than that in the technology using magnetism, and it is possible to improve convenience for the doctors and the like. The blood vessel 3D model 4 is generated by using the radio wave transmission type marker 616, and thus, it is possible to relatively easily specify the correspondence between the blood vessel 3D model 4 and the guide wire 3.

In the present embodiment, the radio wave transmission portion and the radio wave reception portion may be exchanged. That is, the guide wire 3 may be provided with a radio wave reception antenna that receives radio waves, and a plurality of radio wave transmission antennas that transmit radio waves may be provided around the subject SU. In this case, the device indicated by reference numeral 612 is a radio wave reception device, and the device indicated by reference numeral 614 is a radio wave transmission device.

Second Embodiment

A second embodiment will be described with reference to FIGS. 5 to 8. In each of the following embodiments including the present embodiment, a difference from the first embodiment will be mainly described. In the present embodiment, an ultrasound imaging device is used to implement generation of the blood vessel 3D model 4 and detection of the position of the guide wire 3.

Figure 5:
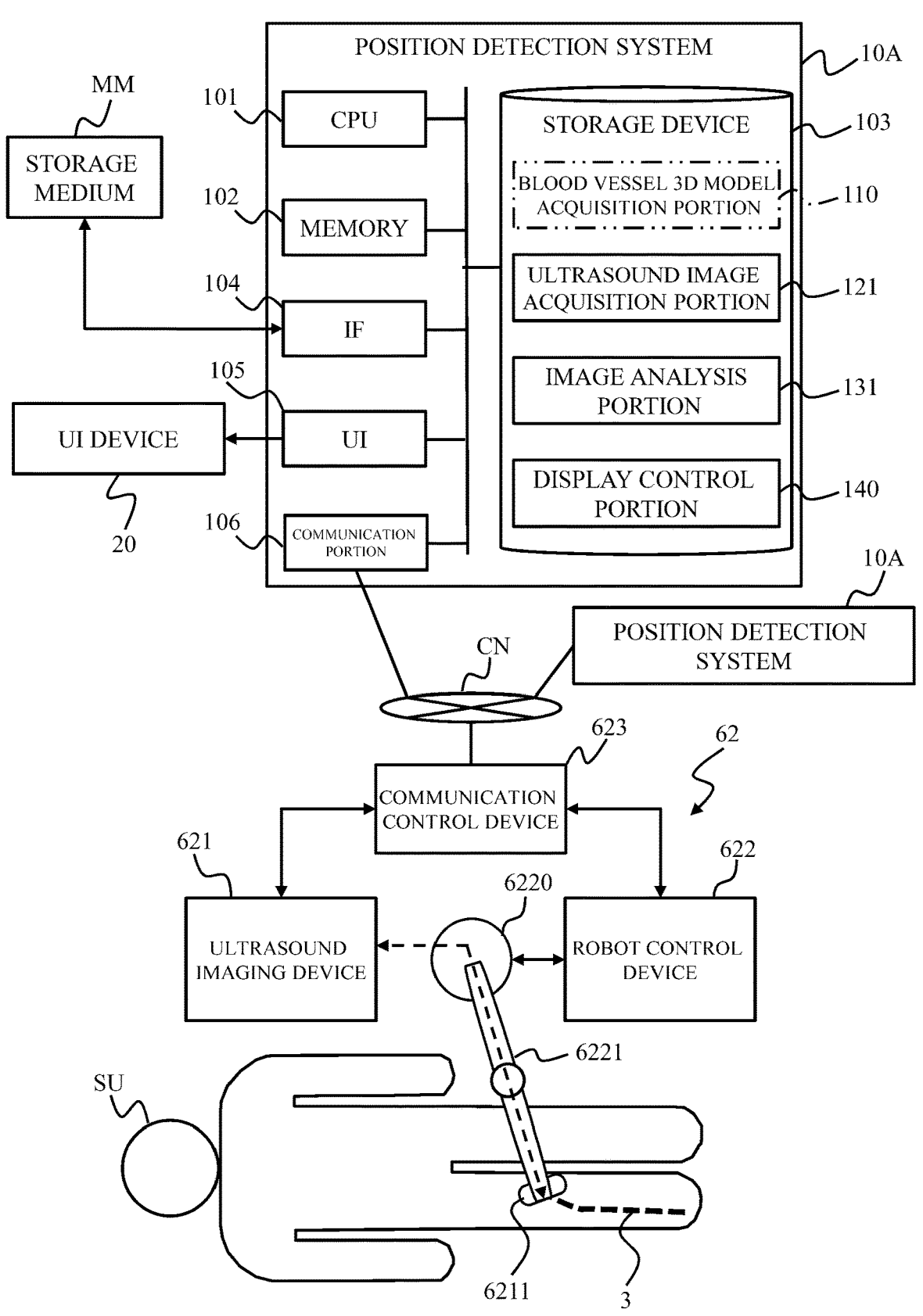
FIG. 5 is an explanatory diagram illustrating an example of configuration of a second embodiment.

FIG. 5 illustrates an example of a configuration of the method (function) 15 for detecting the position of the guide wire 3 by using an ultrasound echo image. In the present embodiment, for example, at least one position detection system 10A and a sensing system 62 using ultrasound waves are provided. The sensing system 62 using ultrasound waves is one example where the function 15 is realized, and includes an ultrasound imaging device 621, a robot control device 622, and a communication control device 623, for example.

The ultrasound imaging device 621 transmits ultrasound waves from an ultrasound probe 6211 toward the subject SU, and generates an image (ultrasound echo image), based on a reflected wave from the subject SU. The robot control device 622 controls an operation of a robot 6220. The robot 6220 is formed as a six-axis robot, and a distal end of an arm 6221 is pivotably attached with the ultrasound probe 6211.

The communication control device 623 connects the ultrasound imaging device 621 and the robot control device 622 to the position detection system 10A via the communication network CN.

The position detection system 10A includes an ultrasound image acquisition portion 121, an image analysis portion 131, and a display control portion 140, for example. The position detection system 10A may or not may include the blood vessel 3D model acquisition portion 110. This is because, in the present embodiment, it is possible to generate the blood vessel 3D model 4 by the ultrasound image acquisition portion 121 while automatically operating the ultrasound probe 6211.

The ultrasound image acquisition portion 121 of the position detection system 10A acquires an ultrasound echo image from the ultrasound imaging device 621 while controlling the robot control device 622. The image analysis portion 131 recognizes the position and the direction of the guide wire 3 by analyzing the acquired ultrasound echo image. The ultrasound image acquisition portion 121 controls the operation of the robot 6220, based on an analysis result by the image analysis portion 131, and causes the ultrasound probe 6211 to track the distal end of the guide wire 3.

Figure 6:
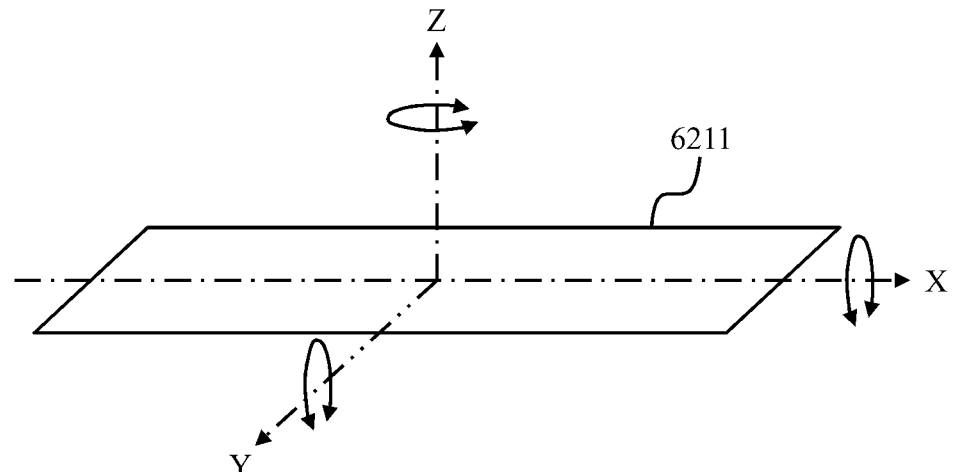
FIG. 6 is an explanatory diagram illustrating a movable range of an ultrasound probe.

FIG. 6 is an explanatory diagram illustrating a pivot range of the ultrasound probe 6211. The ultrasound probe 6211 is pivotable in both directions around central axes, that is, an X-axis, a Y-axis, and a Z-axis. The robot 6220 smoothly moves the ultrasound probe 6211 while pressing the ultrasound probe 6211 provided at the distal end of the arm 6221 against a skin of the subject SU with any force.

FIG. 7 is a flowchart illustrating a blood vessel 3D model generation process and a guide wire position display process according to the present embodiment. In the present embodiment, the position of the guide wire 3 is detected and displayed while the blood vessel 3D model 4 is generated (or updated).

The ultrasound image acquisition portion 121 of the position detection system 10A acquires an ultrasound echo image from the ultrasound imaging device 621 while controlling the robot 6220 (S31). The image analysis portion 131 of the position detection system 10A analyzes the acquired ultrasound echo image to detect the position of the distal end of the guide wire 3 (S32) and further detect the direction of the distal end of the guide wire 3 (S32).

According to the analysis result of the image analysis portion 131, the ultrasound image acquisition portion 121 controls the position of the ultrasound probe 6211 via the robot 6220 so that the ultrasound probe 6211 tracks the distal end of the guide wire 3 (S34).

The image analysis portion 131 may generate the blood vessel 3D model 4 of the subject SU in substantially real time from the ultrasound echo image acquired by the ultrasound probe 6211 (S35). If the blood vessel 3D model 4 is created by the ultrasound imaging device 621 or an X-ray CT device before surgery, the created blood vessel 3D model 4 may be automatically updated in step S35 to obtain the blood vessel 3D model 4 in a latest state.

The display control portion 140 of the position detection system 10A displays the position of the guide wire 3 in association with the blood vessel 3D model 4 on the screen (S36), further calculates the operation assist information, and displays such information on the screen (S37).

In the present embodiment configured as described above, the position, the posture, and the pressing force of the ultrasound probe 6211 is automatically controlled by the robot 6220, and further, the ultrasound echo image is analyzed to detect the position and the direction of the guide wire 3 to cause the ultrasound probe 6211 to automatically track the guide wire 3. Therefore, according to the present embodiment, it is possible to detect the position and the like of the guide wire 3 and display the same in association with the blood vessel 3D model 4 while the blood vessel 3D model 4 is generated and updated.

Figure 8:
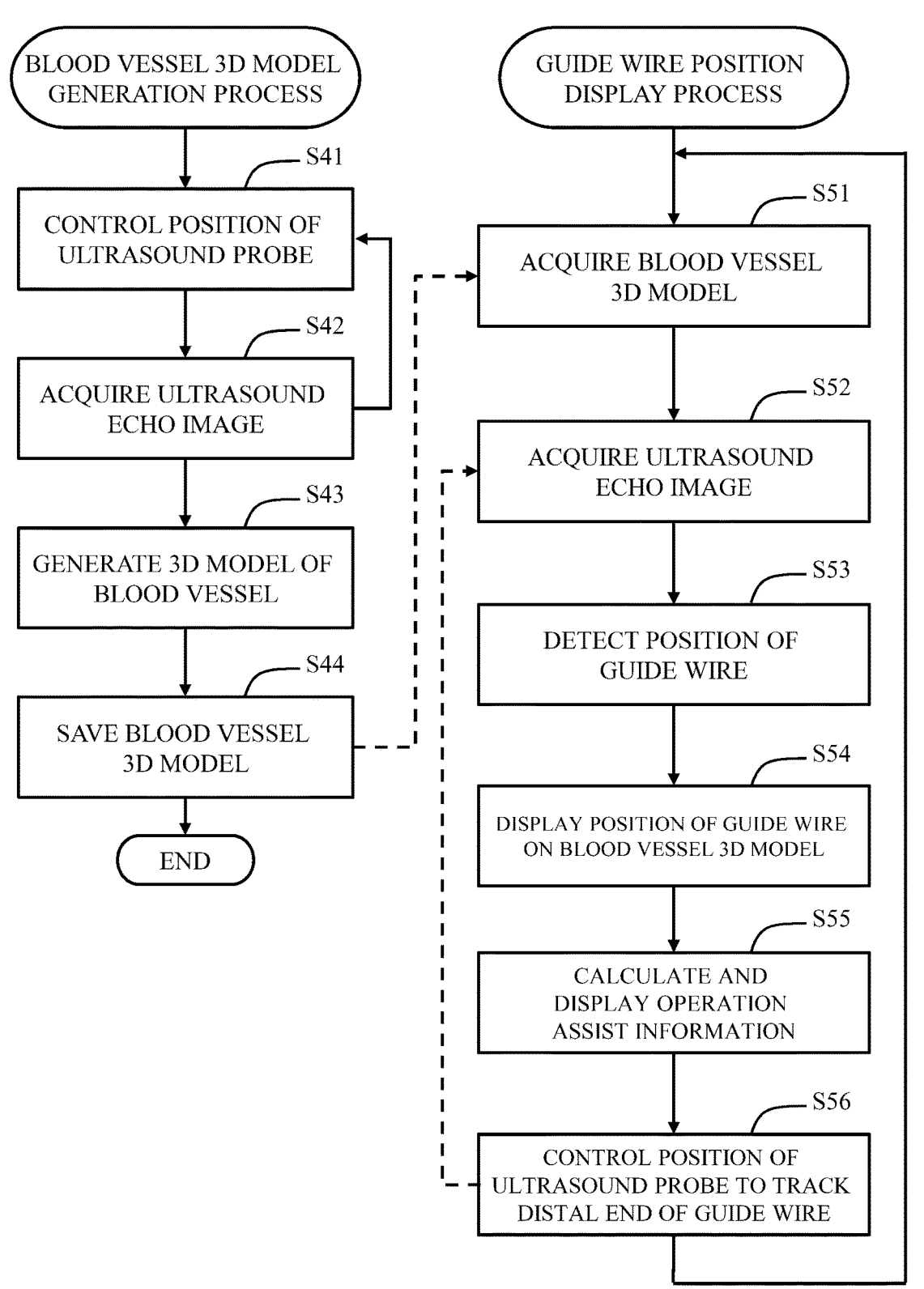

FIG. 8 is a flowchart relating to a modification of the present embodiment. In the present modification, the blood vessel 3D model 4 is generated and saved in advance.

While controlling the position of the ultrasound probe 6211 (S41), the position detection system 10A acquires the ultrasound echo image from the ultrasound imaging device 621 (S42), generates the blood vessel 3D model 4, and saves such a model in the storage device 103 (S43, S44).

When the surgery starts, the blood vessel 3D model acquisition portion 110 of the position detection system 10A acquires the blood vessel 3D model 4 saved in step S44 (S51). The ultrasound image acquisition portion 121 acquires the ultrasound echo image from the ultrasound imaging device 621 via the communication control device 623, the communication network CN, and the like (S52). The image analysis portion 131 detects the position of the guide wire 3 from the acquired ultrasound echo image (S53).

The display control portion 140 displays the position of the guide wire 3 on the blood vessel 3D model 4 (S54), and calculates the operation assist information to display such information on the screen (S55). The ultrasound image acquisition portion 121 calculates the position of the ultrasound probe 6211 to track the distal end of the guide wire 3 and transmits the calculated position to the robot control device 622 (S76). The robot control device 622 controls the robot 6220, based on an instruction from the ultrasound image acquisition portion 121, and causes the ultrasound probe 6211 to track the distal end of the guide wire 3.

Third Embodiment

A third embodiment will be described with reference to FIGS. 9 to 11. In the present embodiment, the position of the guide wire 3 is detected by using a vascular endoscope that captures an image inside the blood vessel.

Figure 9:
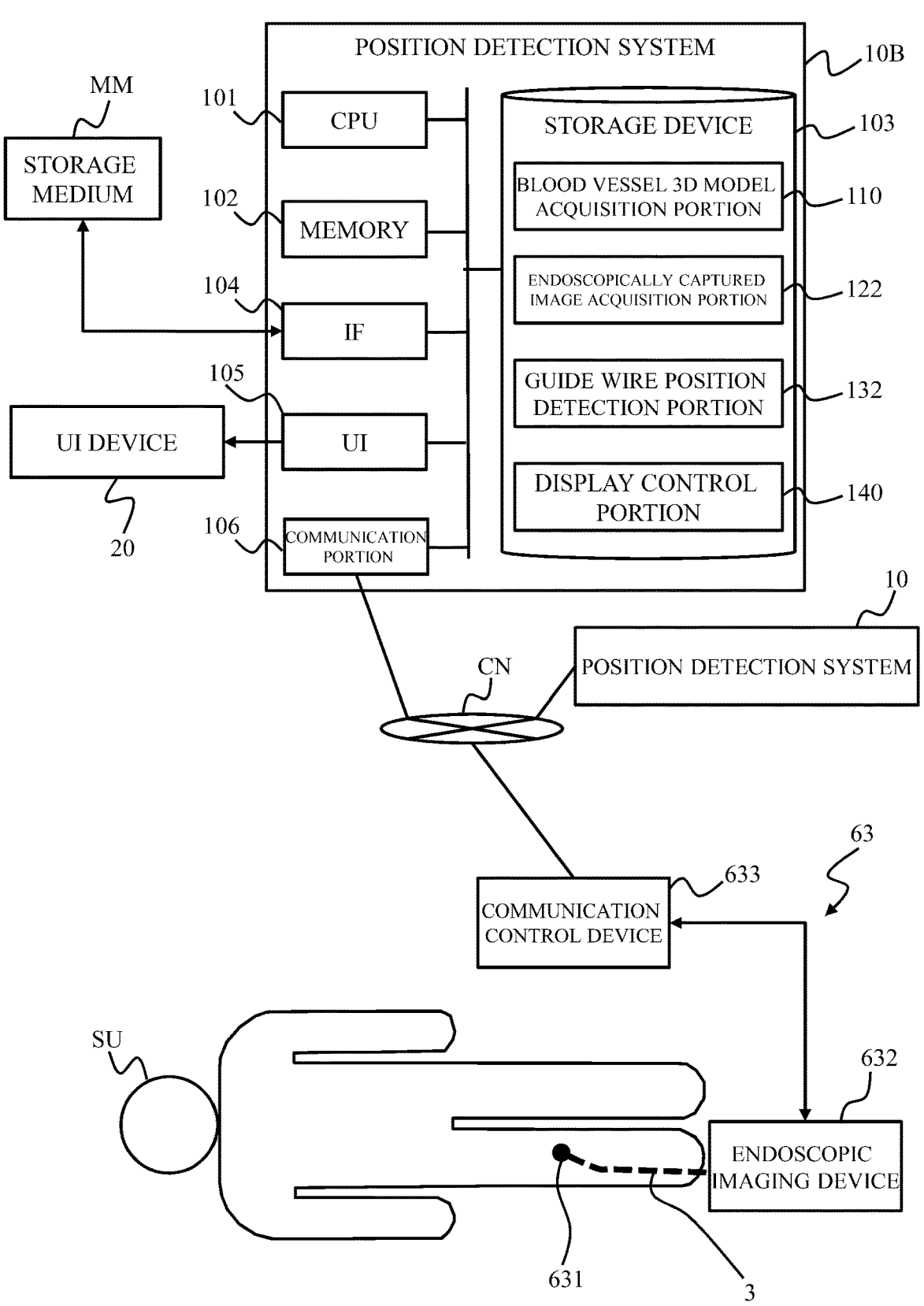
FIG. 9 is an explanatory diagram illustrating an example of a configuration of a third embodiment.

FIG. 9 illustrates an example of a configuration of a method (function) 16 for detecting the position of the guide wire 3 by using a vascular endoscope 631. In the present embodiment, for example, at least one position detection system 10B and a sensing system 63 using a vascular endoscope are provided.

The sensing system 63 using a vascular endoscope is one example where the function 16 is realized. The sensing system 63 includes the vascular endoscope 631, an endoscopic imaging device 632, and a communication control device 633, for example. The vascular endoscope 631 may be of any type. For example, an optical system using for capturing an image with visible light, a system using a near infrared ray, a system using magnetism, a system using radio waves, and a system using ultrasound waves may be employed for the vascular endoscope 631.

The position detection system 10B of the present embodiment includes an endoscopically captured image acquisition portion 122 and a guide wire position detection portion 132. The endoscopically captured image acquisition portion 122 obtains an image captured by the vascular endoscope 631 provided at the distal end of the guide wire 3 via the endoscopic imaging device 632, the communication control device 633, the communication network CN, and the like.

The guide wire position detection portion 132 compares a characteristic of a shape of the obtained blood vessel 3D model 4 and a characteristic of a shape obtained from the image obtained by the endoscope 631 to detect at which location within the blood vessel 3D model 4 the distal end of the guide wire 3 is located.

Figure 10:
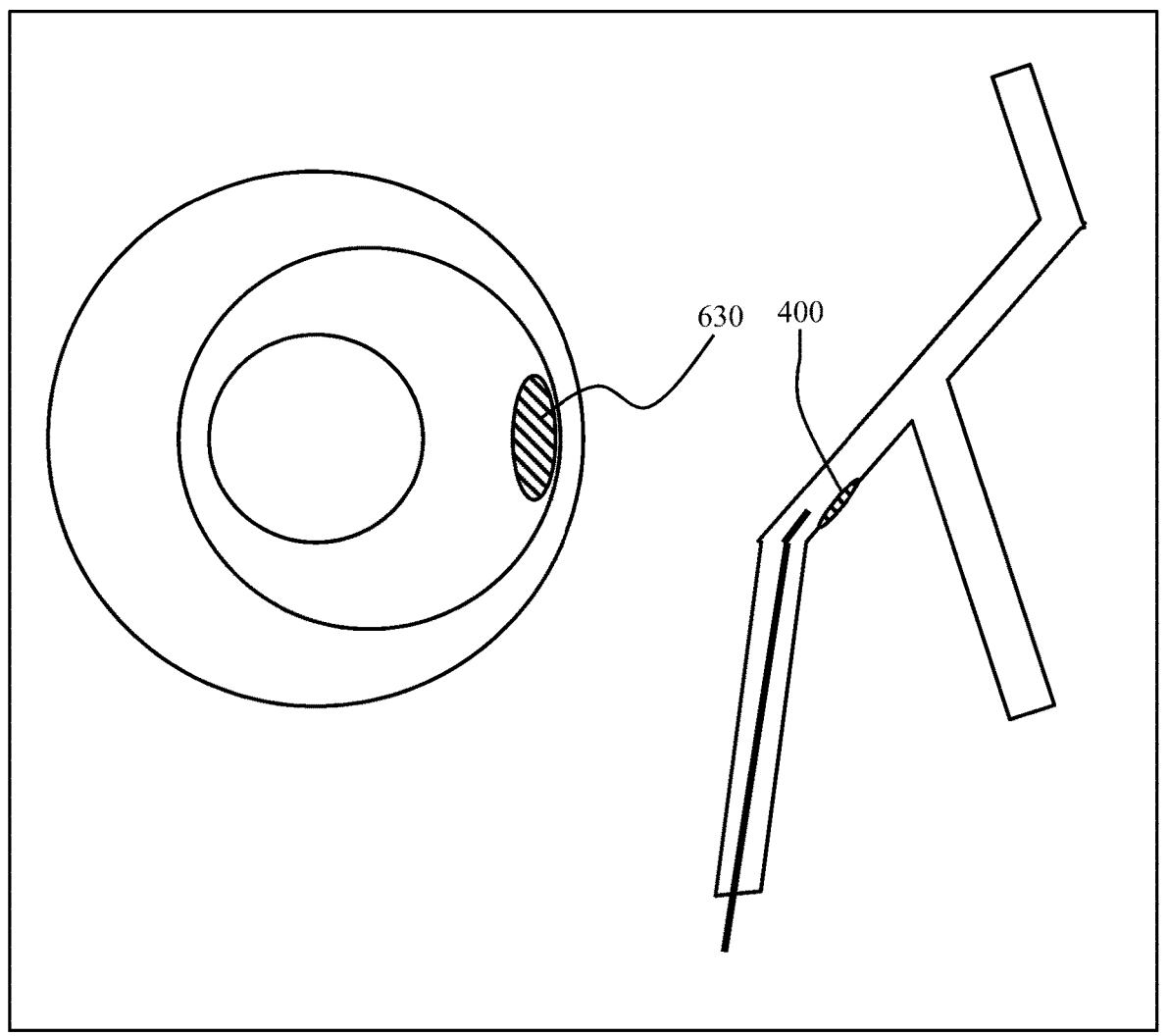
FIG. 10 is an explanatory diagram illustrating a state in which a characteristic point of a blood vessel obtained by a vascular endoscope and a characteristic point of a blood vessel 3D model are collated.

FIG. 10 illustrates a state in which a characteristic point 630 of a blood vessel obtained by a vascular endoscope 631 and a characteristic point 400 extracted from the blood vessel 3D model 4 are compared for collation.

Figure 11:
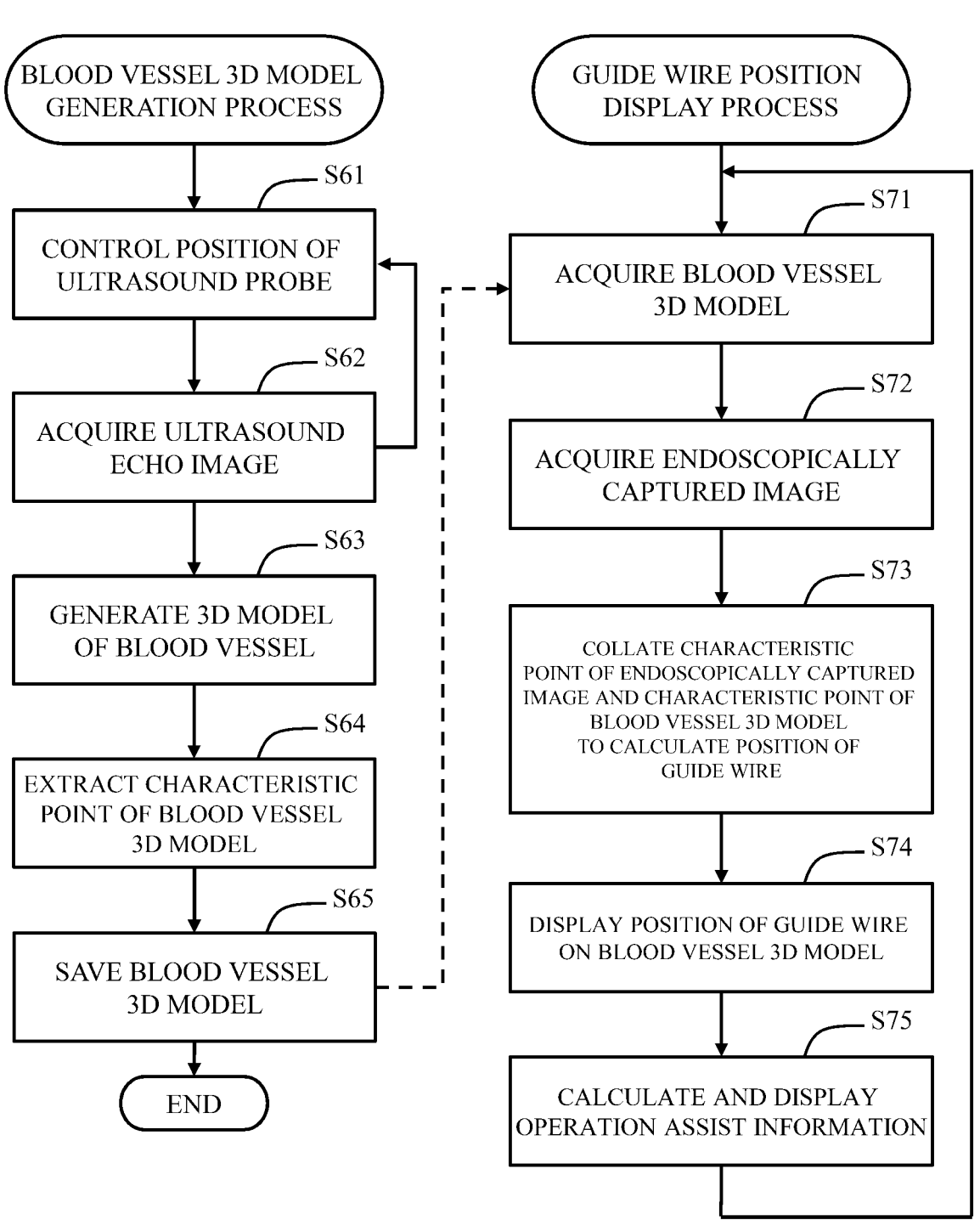

FIG. 11 is a flowchart illustrating a blood vessel 3D model generation process and a guide wire position display process. Similarly to the description with reference to FIG. 8, while controlling the position of the ultrasound probe (S61), the position detection system 10B acquires the ultrasound echo image (S62), generates the blood vessel 3D model 4, and saves such a model in the storage device 103 (S63). When generating or saving the blood vessel 3D model 4, the position detection system 10B extracts the characteristic point 400 provided in the blood vessel 3D model 4 and saves the extracted characteristic point 400 in association with the blood vessel 3D model 4 (S65). Step S65 is an example of a "blood vessel characteristic point extraction portion". Step S65 may be executed by the blood vessel 3D model acquisition portion 110, for example. In this case, it is possible to consider the blood vessel 3D model acquisition portion 110 as an example of a "blood vessel characteristic point extraction portion".

Here, the characteristic point 400 of the blood vessel 3D model 4 includes a situation of the blood vessel, for example. The situation of the blood vessel includes a shape of a blood vessel, a state of an inner wall of a blood vessel, and a color of an inner wall of a blood vessel, for example. Some of the characteristic points may depend on a system (image pickup principle) of the vascular endoscope 631. That is, if it is possible to calculate parameters including a transmittance of an electromagnetic wave, an attenuation rate, a refractive index, and the like from a shape of the blood vessel 3D model 4, an arrangement of an internal organ of the subject SU, and the like, such parameters may be employed for the characteristic point of the blood vessel 3D model 4.

The blood vessel 3D model acquisition portion 110 of the position detection system 10B acquires the blood vessel 3D model 4 saved in step S65 (S71). The endoscopically captured image acquisition portion 122 acquires an endoscopically captured image from the vascular endoscope 631 via the communication control device 633, the communication network CN, and the like (S72). The guide wire position detection portion 132 compares the characteristic point 630 obtained from the acquired endoscopically captured image and the characteristic point 400 provided in the blood vessel 3D model 4 to detect the position of the guide wire 3 (S73). The guide wire position detection portion 132 that executes step S73 or step S73 is an example of a "comparison portion".

The display control portion 140 displays the position of the guide wire 3 on the blood vessel 3D model 4 (S74), and calculates the operation assist information and displays such information on the screen (S75).

In the present embodiment configured as described above, when the characteristic point 630 within the blood vessel acquired from the vascular endoscope 631 and the characteristic point 400 extracted from the blood vessel 3D model 4 created in advance are compared and collated, it is possible to detect the position of the guide wire 3. Therefore, in the present embodiment, it is not necessary to arrange a marker in the subject SU or arrange a sensor around the subject SU, and thus, it is possible to relatively easily detect the position of the guide wire 3 and display such a position on the blood vessel 3D model 4.

Fourth Embodiment

A fourth embodiment will be described with reference to FIGS. 12 and 13. In the present embodiment, the position of the guide wire 3 is detected based on a feed rate of the guide wire 3 to the blood vessel.

Figure 12:
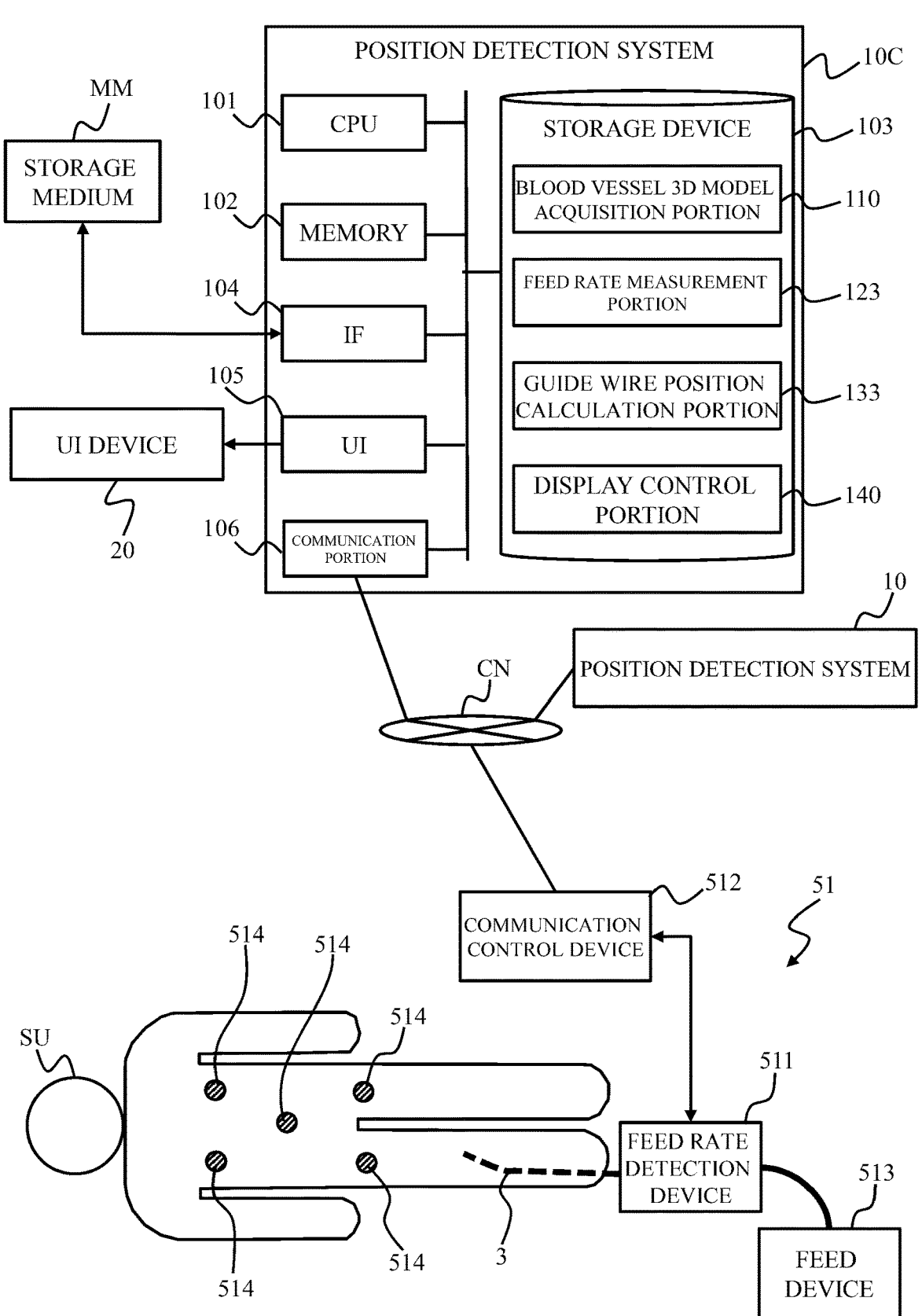
FIG. 12 is an explanatory diagram illustrating an example of a configuration of a fourth embodiment.

FIG. 12 illustrates an example of a configuration of a method (function) 13 for detecting the position of the guide wire 3 from the feed rate of the guide wire 3. In the present embodiment, for example, at least one position detection system 10C and a sensing system 51 according to a feed rate detection scheme are provided.

The sensing system 51 according to the feed rate detection scheme is an example where the function 13 is realized. The sensing system 51 may include a feed rate detecting device 511, a communication control device 512, and a feed device 513, for example. If the feed device 513 is not provided, the guide wire may be manually fed.

The feed rate detecting device 511 detects a feed rate of the guide wire 3 inserted into the blood vessel, and transmits the detected feed rate to a feed rate measurement portion 123 of the position detection system 10C via the communication control device 512. The feed rate is measured as a distance from a point where the guide wire 3 is inserted into the blood vessel. The scheme of detecting the feed rate of the guide wire 3 is not limited. For example, the feed rate may be detected by using a magnetic sensor, an optical sensor, a rotary encoder, or the like.

The feed device 513 is a device that automatically feeds the guide wire 3 into the blood vessel of the subject SU, and may be configured as a guide wire feeding robot. If the feed device 513 is used, the feed rate detecting device 511 may be provided in the feed device 513.

The position detection system 10C includes a feed rate measurement portion 123 and a guide wire position calculation portion 133. The feed rate measurement portion 123 receives a signal from the feed rate detecting device 511. The guide wire position calculation portion 133 calculates, based on the feed rate of the guide wire 3 into the blood vessel and the blood vessel 3D model 4 acquired by the blood vessel 3D model acquisition portion 110, in which part of the blood vessel 3D model 4 the distal end of the guide wire 3 is located.

Figure 13:
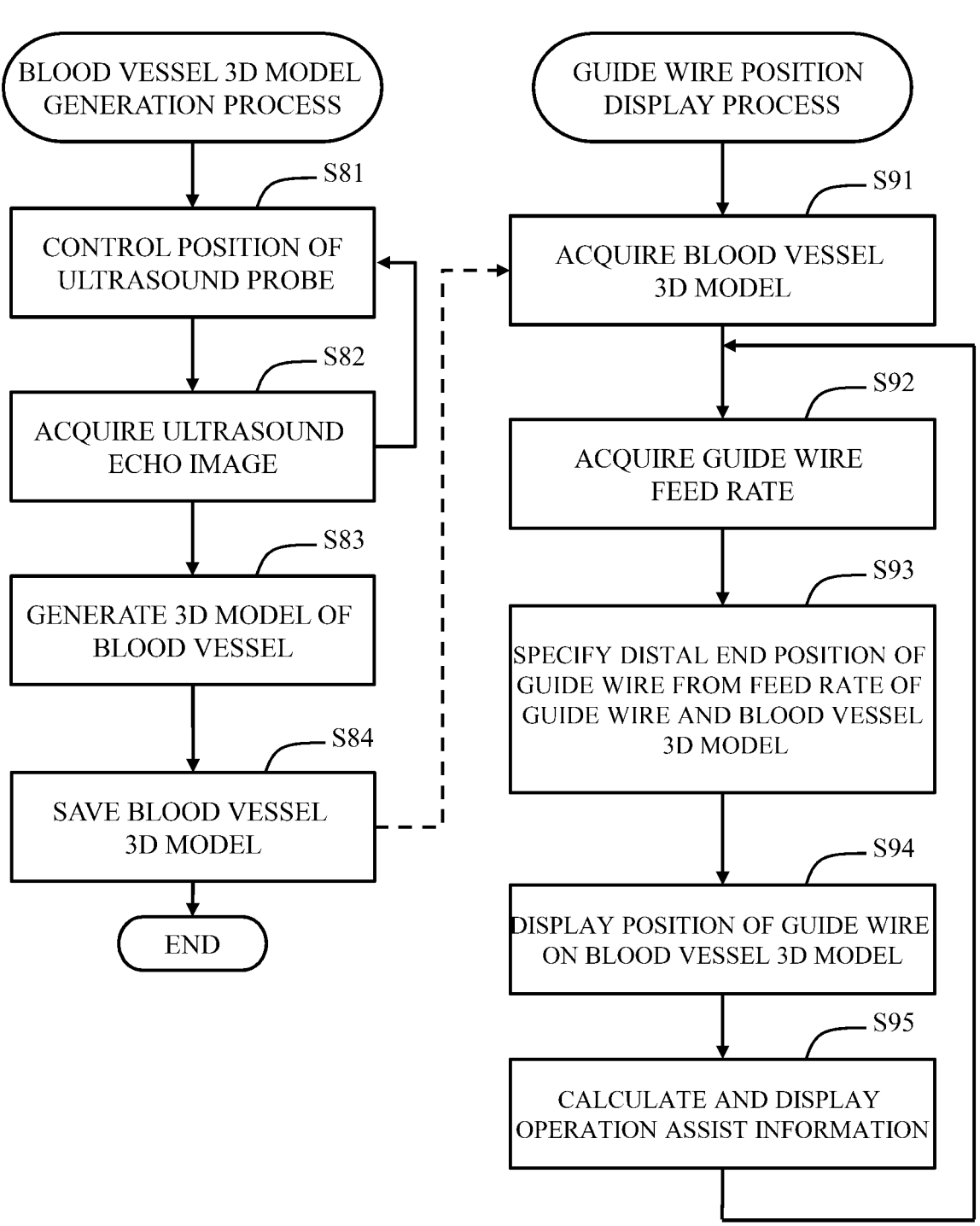

FIG. 13 is a flowchart illustrating a blood vessel 3D model generation process and a guide wire position display process according to the present embodiment.

In the blood vessel 3D model generation process, by using an unillustrated ultrasound imaging device or the like, the ultrasound echo image is acquired while controlling the position of the ultrasound probe (S81, S82), and the blood vessel 3D model 4 is generated and saved (S83, S84).

The blood vessel 3D model acquisition portion 110 of the position detection system 10C acquires the generated blood vessel 3D model (S91), and the feed rate measurement portion 123 of the position detection system 10C acquires the feed rate of the guide wire 3 (S92).

The guide wire position calculation portion 133 of the position detection system 10C compares the feed rate of the guide wire 3 and the blood vessel 3D model to calculate in which part of the blood vessel 3D model the distal end of the guide wire 3 is located (S93). When a reference point at which the feed rate of the guide wire 3 is measured and a reference point of the blood vessel 3D model 4 are aligned, the guide wire position calculation portion 133 may specify, from a length of the guide wire 3 fed into the blood vessel, a predetermined range in which the distal end of the guide wire exists.

The display control portion 140 displays the position of the guide wire 3 on the blood vessel 3D model 4 on the screen (S94), and generates the operation assist information to display such information on the screen (S95).

In the present embodiment configured as described above, it is possible to detect the position of the distal end of the guide wire 3, based on the feed rate of the guide wire 3 into the blood vessel and the blood vessel 3D model 4. The guide wire 3 deflects when traveling in the blood vessel, and thus, the guide wire position calculation portion 133 may predict an amount of deflection, based on the blood vessel 3D model 4, and correct the feed rate with the predicted amount of deflection.

In the present embodiment configured as described above, the position of the distal end of the guide wire 3 is detected from the feed rate of the guide wire 3 into the blood vessel and the blood vessel 3D model 4, and thus, it is not necessary to arrange a marker in the subject SU or arrange a sensor around the subject SU.

Fifth Embodiment

Figure 14:
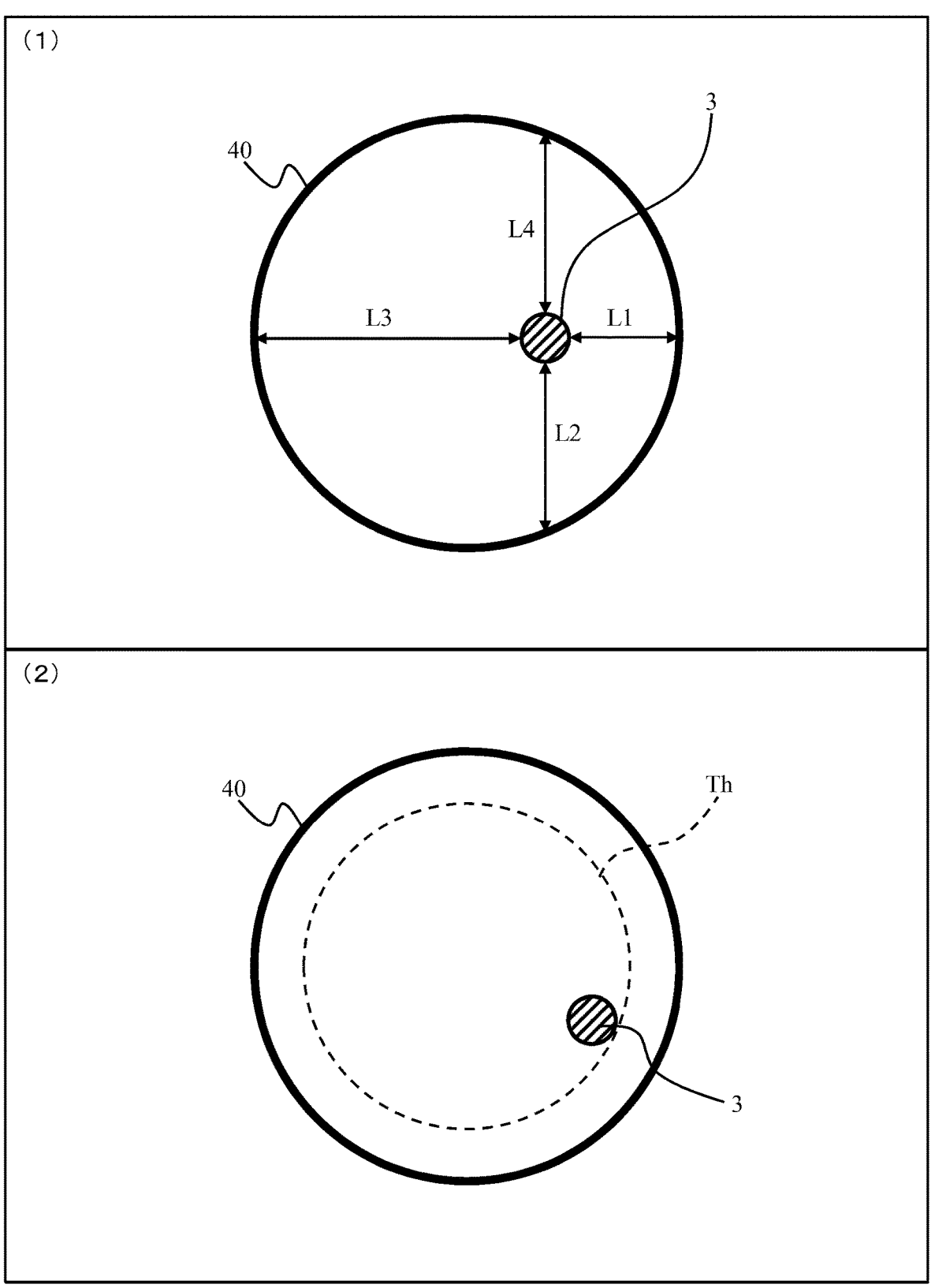
FIG. 14 is an example of a screen for displaying a positional relationship between a blood vessel and a guide wire according to a fifth embodiment.

With reference to FIG. 14, a fifth embodiment will be described. In the present embodiment, an example of the operation assist information by the display control portion 140 will be described.

As illustrated in FIG. 14(1), the display control portion 140 may quantify and display the positional relationship between the blood vessel 40 and the guide wire 3.

As illustrated in FIG. 14(2), the display control portion 140 may also display, together with the guide wire 3, a threshold value Th set to a position separated from the inner wall of the blood vessel 40 by a predetermined distance. When the guide wire 3 borders on the threshold value Th, the display control portion 140 may output an alarm on the screen.

In the present embodiment configured as described above, it is possible to display not only the correspondence between the guide wire 3 and the blood vessel 3D model 4 but also the operation assist information together on the screen, and thus, it is possible to improve convenience for the doctor and the like. If the guide wire 3 borders on the threshold value Th, an alarm is output, and thus, it is possible to enhance the safety of operation by the doctor and the like. It is noted that FIG. 14 describes the case where the transverse cross section of the blood vessel is displayed, but disclosed embodiments are not limited to this, and a longitudinal cross section of the blood vessel may also be displayed by quantifying the positional relationship with the guide wire and a threshold value may also be displayed.

Sixth Embodiment

Figure 15:
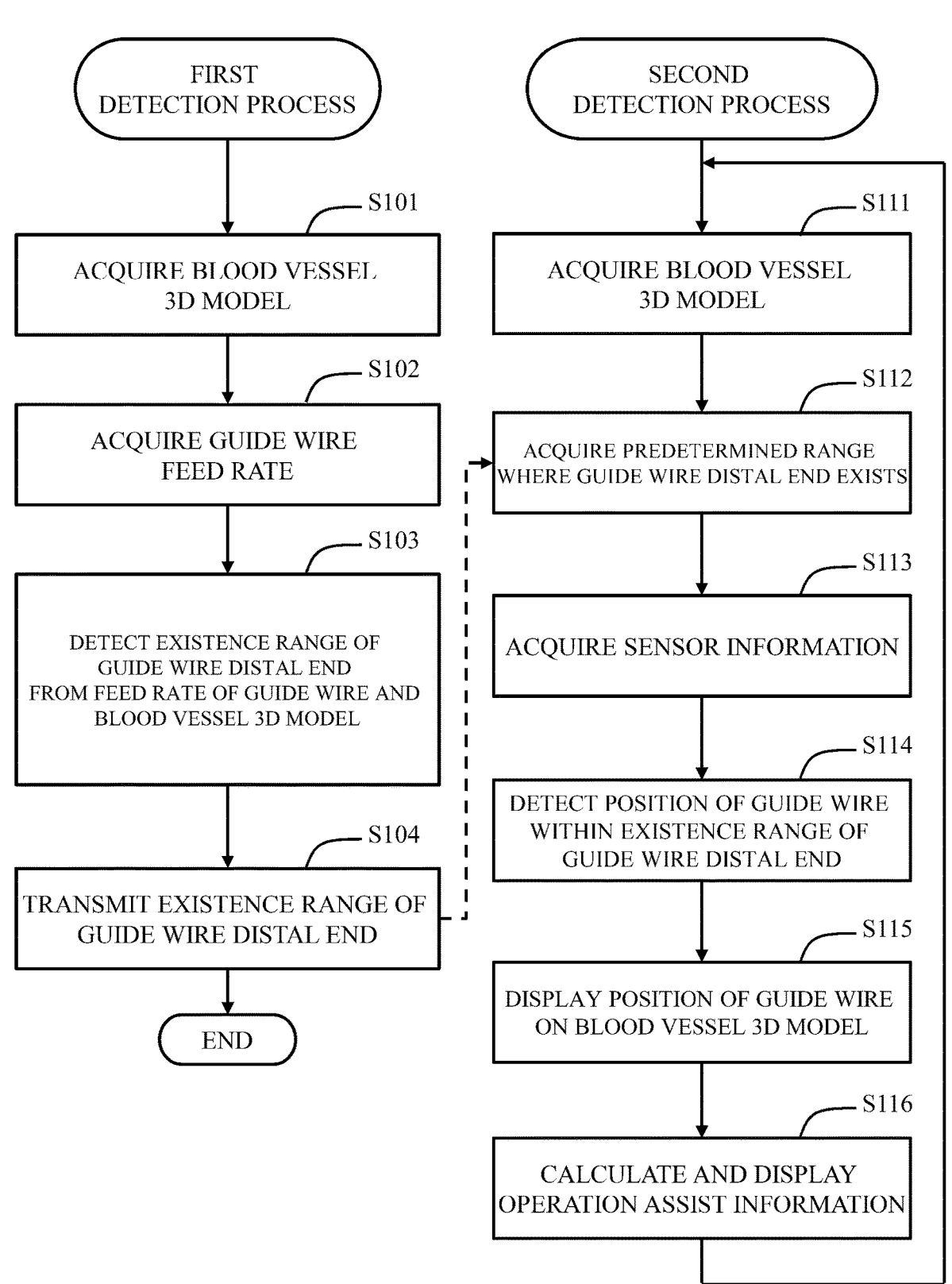
FIG. 15 is a flowchart of a guide wire position display process according to a sixth embodiment.

With reference to FIG. 15, a sixth embodiment will be described. In the present embodiment, a plurality of different detection methods are used to detect stepwise the position of the guide wire 3 in the blood vessel.

FIG. 15 is a flowchart illustrating a first detection process and a second detection process. As described in FIG. 1, the first detection process is executed by the first detection portion 11 and the second detection process is executed by the second detection portion 12. In the present embodiment, as an example of the first detection portion 11, a method based on the feed rate of the guide wire 3 described with reference to FIG. 12 will be described. The second detection portion 12 may be a method based on the radio wave described in FIG. 2, may be a method based on the ultrasound imaging device described in FIG. 5, or a method based on the vascular endoscope described in FIG. 9.

The first detection portion 11 reads the blood vessel 3D model 4 created and saved in advance (S101), and further acquires the feed rate of the guide wire 3 (S102). The first detection portion 11 detects a predetermined range in which the distal end of the guide wire 3 is located, based on the blood vessel 3D model 4 and the feed rate of the guide wire 3 (S103). The first detection portion 11 transmits the detected predetermined range to the second detection portion 12 (S104).

The second detection portion 12 acquires the blood vessel 3D model 4 (S111), and acquires a predetermined range in which the distal end of the guide wire may possibly exist from the first detection portion 11 (S112).

The second detection portion 12 acquires the information on the sensor 6 corresponding to each of the methods (functions) 14 to 16 (S113). That is, if the second detection portion 12 is based on the radio system 14, the second detection portion 12 acquires a reception signal or a transmission signal of a radio wave. If the second detection portion 12 is based on the ultrasound system 15, the second detection portion 12 acquires an ultrasound echo image captured by an ultrasound imaging device. If the second detection portion 12 is based on the blood vessel endoscope system 16, the second detection portion 12 acquires an image captured by the vascular endoscope or a characteristic point of such an image.

The second detection portion 12 detects the position of the distal end of the guide wire 3 according to the detection process of each scheme, within a predetermined range where the distal end of the guide wire may possibly exist (S114). A detection result of the second detection portion 12 is displayed by the display portion 2 (S115, S116). That is, the display portion 2 displays the positional relationship between the blood vessel 3D model 4 and the guide wire 3 on the screen (S115), and creates the operation assist information and displays such information on the screen (S116).

In the present embodiment configured as described above, it is possible to specify stepwise the position of the guide wire 3 by combining a plurality of different detection processes. Therefore, for example, if the first detection process has low accuracy but has a short required time and the second detection process has high accuracy but has a long required time, when the predetermined range specified previously by the first detection process is investigated by the second detection process, it is possible to detect highly accurately and quickly the position of the guide wire 3 in the blood vessel.

It is noted that disclosed embodiments are not limited to the above-described embodiments, and includes various modifications. The above-described embodiments are described in detail to facilitate understanding of disclosed embodiments, and are not necessarily limited to an embodiment including all the described configurations. A part of the configuration of one embodiment may be replaced with a configuration of another embodiment. A configuration of another embodiment may be added to a configuration of a certain embodiment. A part of the configuration of each embodiment may be added with, deleted by, and replaced with another configuration.

Each constituent component in disclosed embodiments may be arbitrarily selected, and the disclosed embodiments including the selected configuration is also included in disclosed embodiments. Further, the configurations described in the claims may be combined in addition to the combinations specified in the claims. Each of the above-mentioned embodiments may be arbitrarily combined.

In the above description, the guide wire is described as an example, but disclosed embodiments are not limited to an object called the guide wire at the time of the present application. Disclosed embodiments can be applied to an object that is inserted into a tube and moves therein, the object needing to be detected in position.

The vascular model may include the affected part (lesion) to be treated. Therefore, the correspondence detection portion may detect the correspondence between the affected part (lesion part) of the blood vessel model and the position of the long medical device.

If the guide wire is used as a long medical device, for example, the correspondence detection portion may detect the correspondence between the blood vessel model (or the affected part of the blood vessel model) and the position of the distal end portion of the guide wire.

If a balloon catheter is used as a long medical device, for example, the correspondence detection portion may detect the correspondence between the blood vessel model (or the affected part of the blood vessel model) and the position of the balloon included in the balloon catheter.

If a cutting balloon is used as a long medical device, for example, the correspondence detection portion may detect the correspondence between the blood vessel model (or the affected part of the blood vessel model) and the position of the cutting blade included in the cutting balloon.

If a stent delivery device is used as a long medical device, for example, the correspondence detection portion may detect the correspondence between the blood vessel model (or the affected part of the blood vessel model) and the position of the stent provided in the stent delivery device.

DESCRIPTION OF REFERENCE NUMERALS

1 Correspondence detection portion
2 Display portion
3 Guide wire
4 Blood vessel model
5 First sensor
6 Second sensor
7 Blood vessel model acquisition portion
10, 10A, 10B, 10C Position detection system
11 First detection portion
12 Second detection portion
13 Feed rate system
14 Radio system
15 Ultrasound system
16 Blood vessel endoscope system
21 First display portion
22 Second display portion
40 Blood vessel
41 Affected part
SU Subject
51 Sensing system using feed rate of guide wire
61 Sensing system using radio waves
62 Sensing system using ultrasound waves
63 Sensing system using vascular endoscope

The invention claimed is:
1. A system for detecting a position of a medical device, the system comprising:
  a sensor;
  a processor programmed to
    acquire a blood vessel model,
    detect a position of the medical device inserted into a blood vessel based on at least one signal received from the sensor, and
    detect a correspondence between the blood vessel model and the position of the medical device; and a display device that displays the position of the medical device in association with the blood vessel model based on the correspondence detected by the processor, wherein in a first detection process, the processor detects a predetermined range including the position of the medical device in the blood vessel model, in a second detection process, the processor detects the correspondence between the blood vessel model and the position of the medical device within the predetermined range that was detected in the first detection process, and the first detection process has a first accuracy and has a first required time, and the second detection process has second accuracy that is higher than the first accuracy and has a second required time that is longer than the first required time.

2. The system according to claim 1, wherein the processor detects the position of the medical device by radio waves as the at least one signal.

3. The system according to claim 2, wherein the sensor includes a plurality of radio wave reception portions arranged around a subject and a radio wave transmission portion provided in the medical device.

4. The system according to claim 2, wherein the sensor includes a plurality of radio wave transmission portions arranged around a subject and a radio wave reception portion provided at a distal end of the medical device.

5. The system according to claim 1, wherein the sensor includes an ultrasound imaging device with an ultrasound probe, and an operation portion that operates the ultrasound probe by pressing the ultrasound probe against a surface of a subject, the processor obtains the blood vessel model generated based on an ultrasound echo image obtained by the ultrasound probe, and the processor recognizes the medical device and the blood vessel from the ultrasound echo image obtained by the ultrasound probe and causes the ultrasound probe to follow a movement of the recognized medical device to detect the correspondence between the blood vessel model and the position of the medical device.

6. The system according to claim 5, wherein the ultrasound probe is caused to follow a movement of a distal end of the medical device to reconstruct the blood vessel model.

7. The system according to claim 1, wherein the processor detects a characteristic point of the blood vessel, and calculates the position of the medical device by comparing the characteristic point and a characteristic point included in the blood vessel model.

8. The system according to claim 1, wherein the processor detects the predetermined range, based on a feed rate of the medical device into the blood vessel.

9. The system according to claim 8, wherein the processor detects the predetermined range, based on the feed rate and a direction of the medical device into the blood vessel.

10. The system according to claim 1, wherein the processor detects the predetermined range, based on a feed rate of the medical device into the blood vessel, and the processor detects a characteristic point of the blood vessel, and calculates the position of the medical device by comparing the characteristic point and a characteristic point included in the blood vessel model.

11. The system according to claim 1, wherein the processor calculates a predetermined value from the correspondence between the blood vessel model and the position of the medical device, and the display device displays the calculated predetermined value in association with the position of the medical device, on the blood vessel model.

12. The system according to claim 11, wherein the predetermined value is a distance between the position of the medical device in the blood vessel model and an inner wall of the blood vessel model.

13. The system according to claim 12, wherein an alarm is output when the predetermined value reaches a previously set threshold value.

14. A method for detecting a position of a medical device, comprising:

a blood vessel model acquisition step of acquiring a blood vessel model;

a correspondence detection step of detecting a position of the medical device inserted into a blood vessel based on at least one signal received from a sensor, and detecting a correspondence between the blood vessel model and the position of the medical device; and a display step of displaying, by a display device, the position of the medical device in association with the blood vessel model based on the detected correspondence, wherein the correspondence detection step includes a first detection step of detecting a predetermined range including the position of the medical device in the blood vessel model, and a second detection step of detecting the correspondence between the blood vessel model and the position of the medical device within the predetermined range that was detected in the first detection step, and the first detection step has a first accuracy and has a first required time, and the second detection step has second accuracy that is higher than the first accuracy and has a second required time that is longer than the first required time.

* * * * *